US008859271B2

(12) United States Patent
Shin et al.

(10) Patent No.: US 8,859,271 B2

(45) Date of Patent: Oct. 14, 2014

(54) THERMAL CYCLING APPARATUS AND METHOD FOR PROVIDING THERMAL UNIFORMITY

(75) Inventors: Hon Siu Shin, Singapore (SG); Jew Kwee Ngui, Singapore (SG); Chee Kiong Lim, Singapore (SG); Ching Ong Lau, Singapore (SG); Lim Hi Tan, Singapore (SG); Yang Hooi Kee, Singapore (SG)

(73) Assignee: Applied Biosystems, LLC, Carlsbad, CA (US)

( * ) Notice: Subject to any disclaimer, the term of this patent is extended or adjusted under 35 U.S.C. 154(b) by 47 days.

(21) Appl. No.: 13/029,085

(22) Filed: Feb. 16, 2011

(65) Prior Publication Data

US 2011/0136219 A1 Jun. 9, 2011

Related U.S. Application Data

(63) Continuation of application No. 12/421,568, filed on Apr. 9, 2009, now abandoned, which is a continuation of application No. 10/448,804, filed on May 30, 2003, now abandoned.

(51) Int. Cl.

| | |
|---|---|
| ***C12M 1/00*** | (2006.01) |
| ***C12M 3/00*** | (2006.01) |
| ***B01L 7/00*** | (2006.01) |

(52) U.S. Cl.

CPC ........... *B01L 7/52* (2013.01); *B01L 2300/0829* (2013.01); *B01L 2300/1822* (2013.01)

USPC .................. 435/303.1; 435/305.1; 435/287.2; 435/288.3; 435/6.12; 136/203; 136/205; 219/386; 219/521

(58) Field of Classification Search

CPC ................ B01L 2300/0829; B01L 2300/1822; B01L 7/52

USPC ............ 435/303.1, 305.1, 287.2, 288.3, 6.12; 136/203, 205; 219/386, 521

See application file for complete search history.

(56) References Cited

U.S. PATENT DOCUMENTS

| | | | | |
|---|---|---|---|---|
| 5,455,175 A | | 10/1995 | Wittwer et al. | |
| 5,525,300 A | | 6/1996 | Danssaert et al. | |
| 5,935,522 A | | 8/1999 | Swerdlow et al. | |
| 6,004,512 A | | 12/1999 | Titcomb et al. | |
| 6,085,833 A | * | 7/2000 | Kimura et al. | ............... 165/185 |
| 6,303,343 B1 | | 10/2001 | Kopf-Sill | |

(Continued)

FOREIGN PATENT DOCUMENTS

| | | |
|---|---|---|
| EP | 1216098 | 7/2003 |
| JP | 2003-107094 | 4/2003 |

(Continued)

OTHER PUBLICATIONS

English translation of Heimberg WO 01/24930.*

(Continued)

*Primary Examiner* — Nathan Bowers

(57) ABSTRACT

An apparatus and method for rapid thermal cycling including a thermal diffusivity plate. The thermal diffusivity plate can provide substantial temperature uniformity throughout the thermal block assembly during thermal cycling by a thermoelectric module. An edge heater can provide substantial temperature uniformity throughout the thermal block assembly during thermal cycling.

35 Claims, 14 Drawing Sheets

(56) References Cited

U.S. PATENT DOCUMENTS

| | | | | |
|---|---|---|---|---|
| 6,334,980 | B1 | 1/2002 | Hayes et al. | |
| 6,337,435 | B1 * | 1/2002 | Chu et al. | 136/242 |
| 6,499,306 | B2 | 12/2002 | Gillen | |
| 6,514,750 | B2 * | 2/2003 | Bordenkircher et al. | 435/286.2 |
| 6,524,830 | B2 | 2/2003 | Kopf-Sill | |
| 6,556,940 | B1 * | 4/2003 | Tretiakov et al. | 702/130 |
| 6,719,949 | B1 | 4/2004 | Barzilai et al. | |
| 2001/0007759 | A1 | 7/2001 | Wittwer et al. | |
| 2002/0029867 | A1 * | 3/2002 | Sauer | 165/80.3 |
| 2002/0030044 | A1 * | 3/2002 | Brown | 219/386 |
| 2002/0046627 | A1 * | 4/2002 | Amita et al. | 75/252 |
| 2002/0179290 | A1 | 12/2002 | Larson | |
| 2002/0185269 | A1 * | 12/2002 | Sato | 165/185 |
| 2003/0072685 | A1 * | 4/2003 | Goldman et al. | 422/102 |
| 2003/0081945 | A1 | 5/2003 | Kusuda | |
| 2004/0072334 | A1 * | 4/2004 | Benett et al. | 435/286.1 |
| 2007/0140926 | A1 | 6/2007 | Heimberg et al. | |
| 2009/0203120 | A1 | 8/2009 | Shin et al. | |

FOREIGN PATENT DOCUMENTS

| | | |
|---|---|---|
| WO | 98/20975 | 5/1998 |
| WO | 01/08800 | 2/2001 |
| WO | 01/24930 | 4/2001 |
| WO | WO-01/24930 A1 * | 12/2001 |
| WO | 2004/105947 | 12/2004 |
| WO | 2004/108288 | 12/2004 |

OTHER PUBLICATIONS

International Search Report for Application No. PCT/US2004/017017 dated Oct. 19, 2004.

* cited by examiner

THERMAL CYCLING APPARATUS AND METHOD FOR PROVIDING THERMAL UNIFORMITY

CROSS REFERENCE TO RELATED APPLICATION

This application is a continuation of application Ser. No. 12/421,568 filed Apr. 9, 2009, which is a continuation of application Ser. No. 10/448,804 filed May 30, 2003, which applications are incorporated herein by reference in their entirety.

FIELD

The present teachings relate to thermal cycling of biological samples. Improvement in thermal cycling can be provided by a thermal diffusivity plate.

INTRODUCTION

In the biological field, thermal cycling can be utilized to provide heating and cooling of reactants in a reaction vessel. Examples of reactions of biological samples include polymerase chain reaction (PCR) and other reactions such as ligase chain reaction, antibody binding reaction, oligonucleotide ligations assay, and hybridization assay. In PCR, biological samples can be thermally cycled through a temperature-time protocol that includes melting DNA into single strands, annealing primers to the single strands, and extending those primers to make new copies of double-stranded DNA. During thermal cycling, it is desirable to maintain thermal uniformity throughout a thermal block assembly so that different sample wells can be heated and cooled uniformly to obtain uniform sample yields. Uniform yields can provide quantification between samples wells.

SUMMARY

According to various embodiments, an apparatus for thermally cycling biological samples can comprise a thermal block assembly for receiving the biological sample; a thermoelectric module coupled to the thermal block assembly; and a heat sink, wherein the heat sink is coupled to the thermoelectric module, wherein the heat sink comprises a base plate, fins, and a thermal diffusivity plate, and wherein the thermal diffusivity plate comprises a different material than the base plate and fins, wherein the thermal diffusivity plate provides substantial temperature uniformity to the thermal block assembly during thermal cycling.

According to various embodiments, an apparatus for thermally cycling biological samples can comprise a thermal block assembly for receiving the biological sample; a thermoelectric module coupled to the thermal block assembly; a heat sink; and a thermal diffusivity plate coupled to the thermoelectric module and the heat sink, wherein the thermal diffusivity plate is positioned between the thermoelectric module and the heat sink, wherein the thermal diffusivity plate has a significantly greater thermal diffusivity than the heat sink.

According to various embodiments, a method for thermally cycling biological samples can comprise contacting a thermoelectric module to a thermal block assembly; heating the thermal block assembly, wherein the thermal block assembly is adapted for receiving the biological sample; and cooling the thermal block assembly, wherein the cooling comprises diffusing heat to a heat sink through a thermal diffusivity plate.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

DESCRIPTION OF VARIOUS EMBODIMENTS

Figure 1:
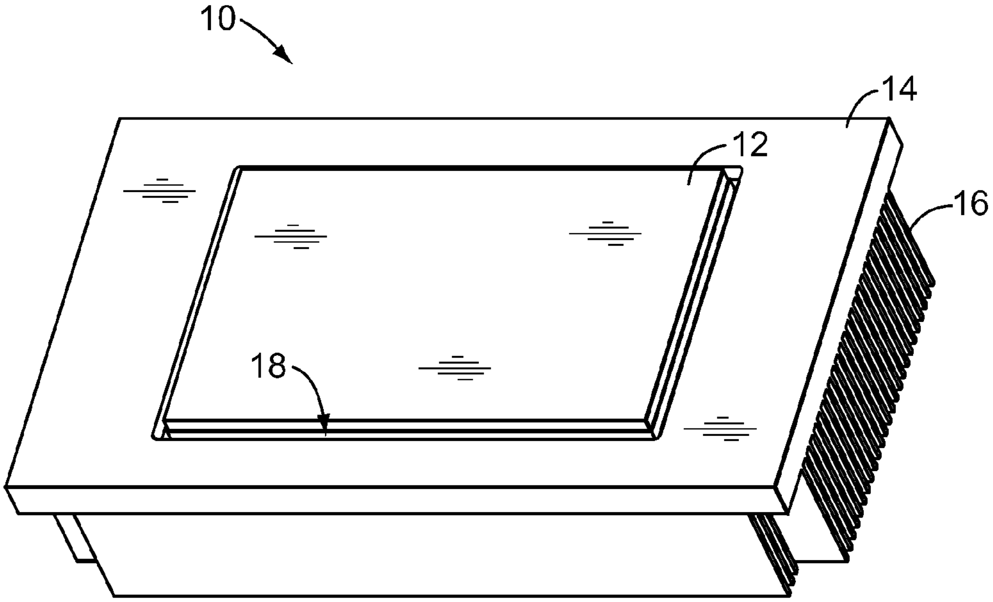
FIG. 1 illustrates various embodiments of a heat sink.

Reference will now be made to various embodiments, examples of which are illustrated in the accompanying drawings. Wherever possible, the same reference numbers are used in the drawings and the description to refer to the same or like parts.

According to various embodiments, the apparatus for thermally cycling biological samples provides heat-pumping into and out of a thermal block assembly, resistive heating of the thermal block assembly, and diffusive cooling of the thermal block assembly. The term "thermal cycling" or grammatical variations of such as used herein refer to heating, cooling, temperature ramping up, and/or temperature ramping down. Thermal cycling during temperature ramping up, when heating the thermal block assembly above ambient (20° C.), can comprise resistive heating of the thermal block assembly and/or pumping heat into the thermal block assembly by the thermoelectric module against diffusion of heat away from the thermal block assembly. Thermal cycling during temperature ramping down, when cooling the thermal block assembly above ambient (20° C.), can comprise pumping heat out of the thermal block assembly by the thermoelectric module and diffusion of heat away from the thermal block assembly against resistive heating.

According to various embodiments, FIGS. 1-5 and FIGS. 14-15 illustrate portions of an apparatus for thermally cycling biological sample. FIG. 1 illustrates heat sink 10, thermal diffusivity plate 12, base plate 14, and fins 16. According to various embodiments, thermal diffusivity plate 12 can be separate from the heat sink 10. According to various embodiments, heat sink 10 can comprise thermal diffusivity plate 12. According to various embodiments, thermal diffusivity plate 12 can comprise copper. According to various embodiments, base plate 14 and fins 16 can comprise aluminum.

Names of metals as used herein such as copper, aluminum, etc. refer to the pure metal, alloys of the metal, amalgams of the metal, or any variation of the metal known in the art of material science.

Figure 5:
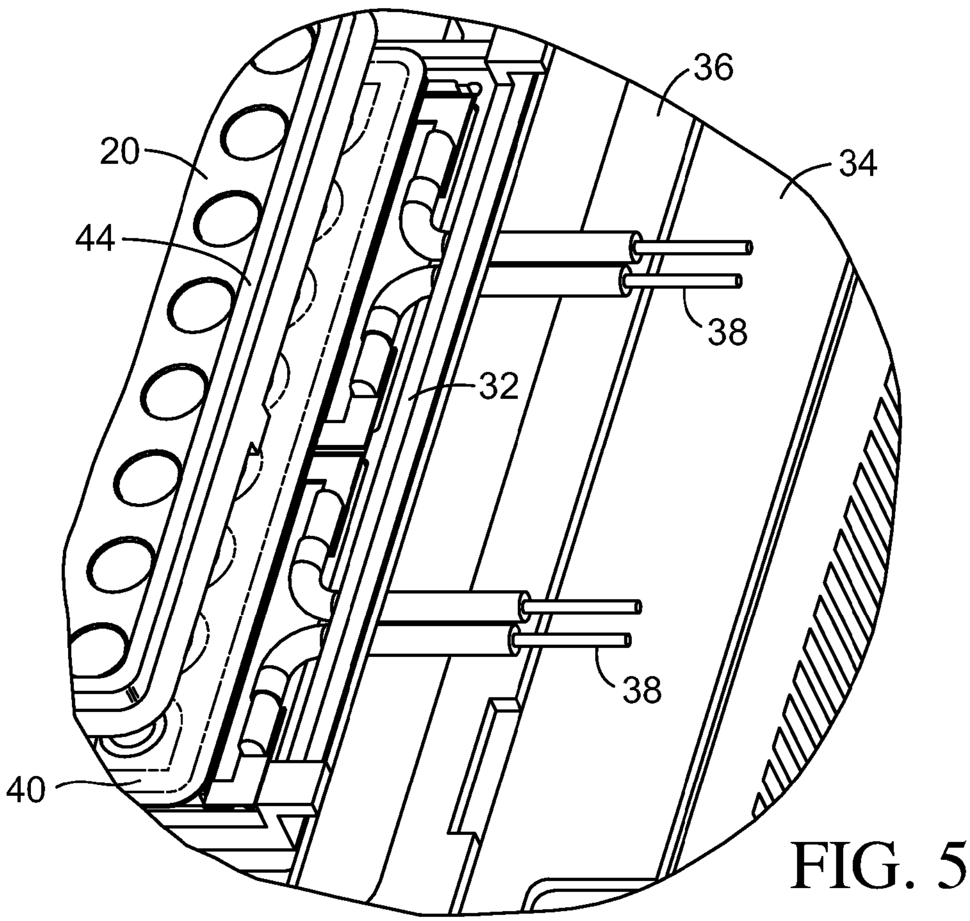
FIG. 5 is a magnified view of a detail of FIG. 4 illustrating various embodiments of the coupling of the edge heater to the thermal block assembly and the coupling of the thermal block assembly to the thermoelectric module.
Figure 5A:
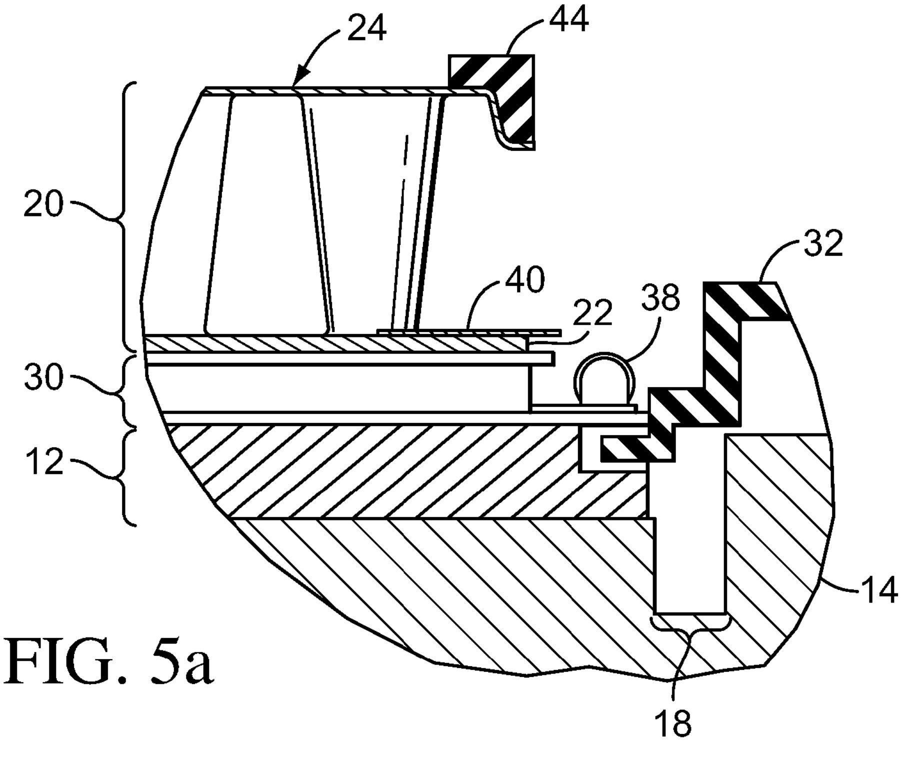
FIG. 5*a* is a cross-sectional view of FIG. 5 illustrating various embodiments of the coupling of the edge heater to the thermal block assembly and the coupling of the thermal block assembly to the thermoelectric module.

According to various embodiments, the thermal diffusivity plate can be constructed of different material than the rest of the heat sink such that the thermal diffusivity plate can have significantly greater thermal diffusivity than the rest of the heat sink. According to various embodiments, the base plate and fins can be constructed of different materials. According to various embodiments, the thermal diffusivity plate can comprise other composite materials that provide thermal diffusivity as known in the art of material science. According to various embodiments, as illustrated in FIG. 1, trench 18 can be positioned around the perimeter of the thermal diffusivity plate and the base plate. According to various embodiments, trench 18, as illustrated in FIG. 5*a* can extend up to the thermoelectric module 30. Trench 18 can limit the amount of heat diffusion away from the thermal block assembly and decrease the heat loss from the area bounded by trench 18. Frame 32 can be constructed of non-conductive material to avoid substantially negating the effect of trench 18.

It can be desirable to reduce the cost and weight of the heat sink while providing significantly greater thermal diffusivity with the thermal diffusivity plate. According to various embodiments, the thermal diffusivity plate can be constructed of copper and the base plate and fins can be constructed of aluminum because copper can weigh more and can be more expensive than aluminum. According to various embodiments, the thermal diffusivity plate, base plate, and fins can be constructed of the same material providing similar thermal diffusivity throughout the heat sink.

"Thermal diffusivity" or "diffusion" of heat or grammatical variations of such as used herein refer to the transport property for transient conduction. Thermal diffusivity can measure the ability of a material to conduct thermal energy relative to its ability to store thermal energy. Materials with greater thermal diffusivity can respond more rapidly to changes in their thermal environment. Thermal diffusivity can be calculated using the formula (1):

$$a = \frac{k}{\rho * C_p} \tag{1}$$

where a is thermal diffusivity which can be measured in square meters per second, k is thermal conductivity which can be measured in watts per meters-Kelvin, $C_p$ is specific heat capacity which can be measured in joules per kilograms-Kelvin, and ρ is density which can be measured in kilograms per cubic meter. As known in the art of material science, there are alternative ways of measuring these thermal properties.

According to various embodiments, the thermal diffusivity plate can comprise copper, silver, gold, or silicone carbide. "Thermal capacitance" as used herein refers to the ability of a material to store thermal energy. It can be desirable to provide a thermal block assembly that can have a significantly lower thermal capacitance so that heat diffuses to the thermal diffusivity plate. Thermal capacitance can be calculated using the formula (2):

$$C_T = \rho \times C_p \tag{2}$$

where $C_T$ is thermal capacitance which can be measured in joules per cubic meter-Kelvin, $C_p$ is specific heat capacity which can be measured in joules per kilograms-Kelvin, and ρ is density which can be measured in kilograms per cubic meter. "Significantly" greater or lower as used herein refers to a thermal diffusivity or thermal capacitance values of at least twenty-five percent greater or lower than the values to which they are compared. Table 1 contains values for each of the aforementioned thermal properties according to various embodiments:

TABLE 1

| Thermal Properties | Aluminum | Copper | Silver | Gold | Mg | Silicone Carbide |
|---|---|---|---|---|---|---|
| k (W/m-K) | 209 | 391 | 419 | 301 | 159 | 300 |
| $C_p$ (J/kg-K) | 900 | 385 | 234 | 132 | 1025 | 640 |
| ρ (kg/m$^3$) | 2700 | 8900 | 10491 | 19320 | 1740 | 3210 |
| a (m$^2$/s) | $8.60 \times 10^{-5}$ | $1.14 \times 10^{-4}$ | $1.71 \times 10^{-4}$ | $1.18 \times 10^{-4}$ | $8.92 \times 10^{-5}$ | $1.46 \times 10^{-4}$ |
| $C_T$ (J/m$^3$-K) | $2.43 \times 10^6$ | $3.43 \times 10^6$ | $2.45 \times 10^6$ | $2.56 \times 10^6$ | $1.78 \times 10^6$ | $2.05 \times 10^6$ |

According to various embodiments, a thermal diffusivity plate constructed of copper, silver, gold, or silicone carbide (for example silicone carbide plated by chemical vapor deposition) can have significantly greater thermal diffusivity than a base plate and fins constructed of aluminum or magnesium. According to various embodiments, a thermal diffusivity plate constructed of copper can have a significantly greater thermal capacitance than a thermal block assembly constructed of silver, gold, or magnesium.

Figure 2:
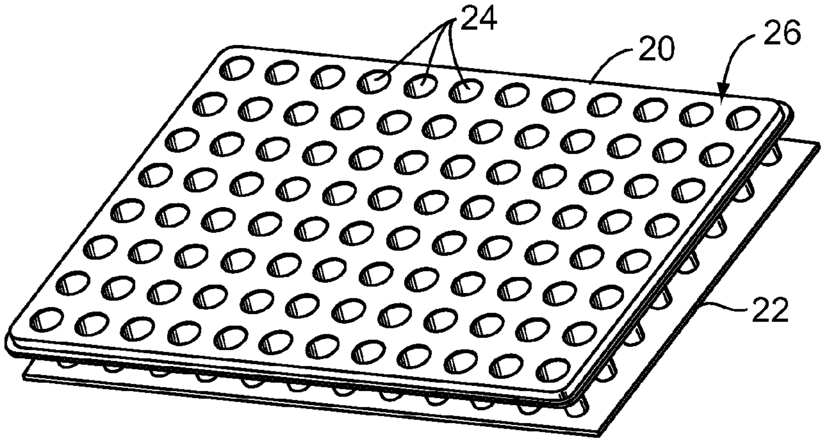
FIG. 2 illustrates various embodiments of a thermal block assembly.

According to various embodiments, FIG. 2 illustrates a thermal block assembly 20 with a plurality of openings 24 and a bottom 22. In this embodiment, the plurality of openings 24 are adapted to receive sample wells to contain the biological samples. The sample wells can be configured into a sample well tray. The top of each sample well can be sealed by a cap, an adhesive film, a heat seal, or a gap pad. According to various embodiments, the thermal block assembly can be adapted to receive and contain the biological sample in a plurality of openings. According to various embodiments, the biological sample can be received and contained by surfaces instead of wells. These surfaces can be separate or integral to the thermal block assembly.

According to various embodiments, the thermal block assembly can comprise at least one of silver, gold, aluminum alloy, silicone carbide, and magnesium. Other materials known in the art of thermal cycling can be used to construct the thermal block assembly. These materials can provide high thermal conductivity.

Figure 3:
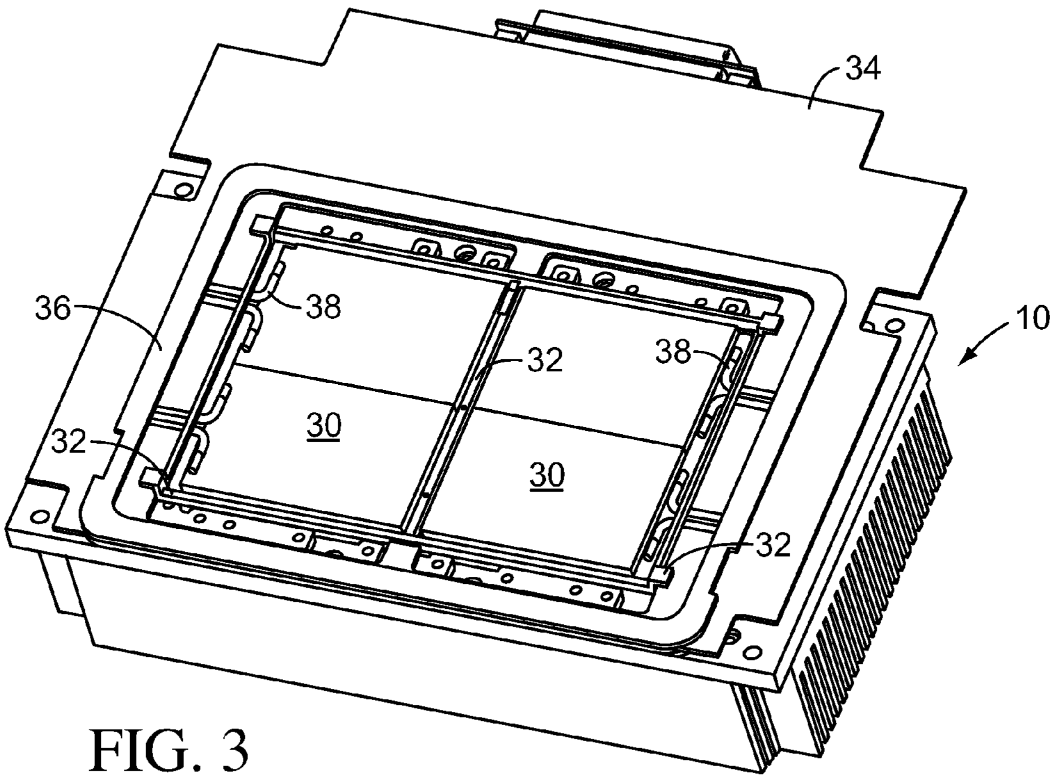
FIG. 3 illustrates various embodiments of a thermoelectric module coupled to a heat sink.

According to various embodiments, FIG. 3 illustrates the heat sink 10 illustrated in FIG. 1 coupled to a thermoelectric module 30. According to various embodiments, thermoelectric module 30 overlaps with thermal diffusivity plate 12. According to various embodiments, either the thermal diffusivity plate or the thermoelectric module can have a larger surface area. As illustrated in FIG. 3, thermoelectric module 30 sits on printed circuit board (PCB) 34 and both portions of the thermoelectric module 30 are lined by frame 32 that can fill the thermoelectric gap between each portion of the thermoelectric module 30 and trench 18. Leads 38 can provide power to the thermoelectric module 30. Gasket 36 can be positioned on PCB 34 and can line both the thermoelectric module 30 and frame 32. According to various embodiments, the gasket can be constructed of material comprising at least one of EPDM Rubber, Silicone Rubber, Neoprame (CR) Rubber, SBR Rubber, Nitrile (NBR) Rubber, Butyl Rubber, Hypalon (CSM) Rubber, Polyurethane (PU) Rubber, and Viton Rubber. According to various embodiments, the frame can be constructed of similar material to the gasket, Ultem® Resin (General Electric Plastics; amorphous thermoplastic polyetherimide), or other suitable material. According to various embodiments, frame 32 can be positioned around the thermoelectric module 30 for alignment with the thermal block assembly 20 and thermal diffusivity plate 12. According to various embodiments, the frame can comprise tabs, as illustrated on the corners of frame 32 in FIG. 3, to facilitate handling of frame 32.

"Thermoelectric module" as used herein refers to Peltier devices, also known as thermoelectric coolers (TEC), that are solid-state devices that function as heat pumps. The Peltier device can comprise two ceramic plates with a bismuth telluride composition in between. When a DC current can be applied heat is moved from one side of the device to the other, where it can be removed with a heat sink and/or a thermal diffusivity plate. The "cold" side can be used to pump heat out of the thermal block assembly. If the current is reversed the device can be used to pump heat into the thermal block assembly. The Peltier devices can be stacked to achieve increase the cooling and heating effects of heat pumping. Peltier devices are known in the art and manufactured by several companies, including Tellurex Corporation (Traverse City, Mich.), Marlow Industries (Dallas, Tex.), Melcor (Trenton, N.J.), and Ferrotec America Corporation (Nashua, N.H.).

Figure 3A:
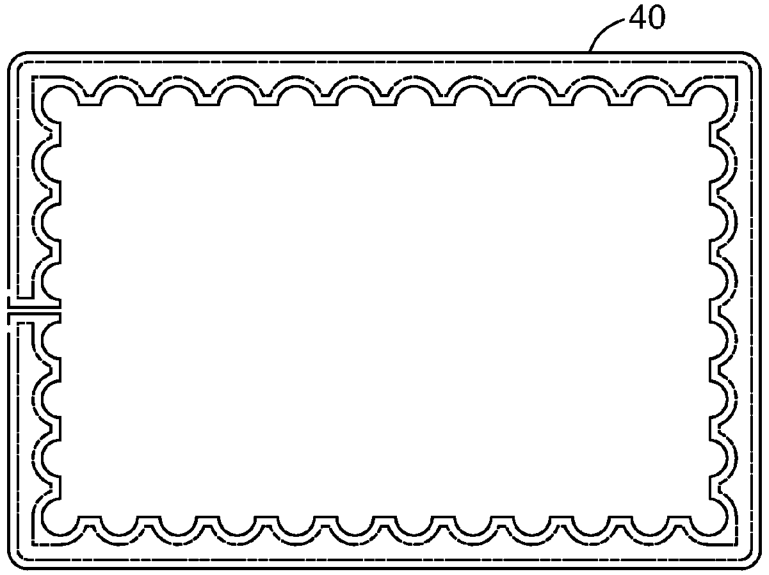
FIG. 3*a* illustrates various embodiments of an edge heater.
Figure 4:
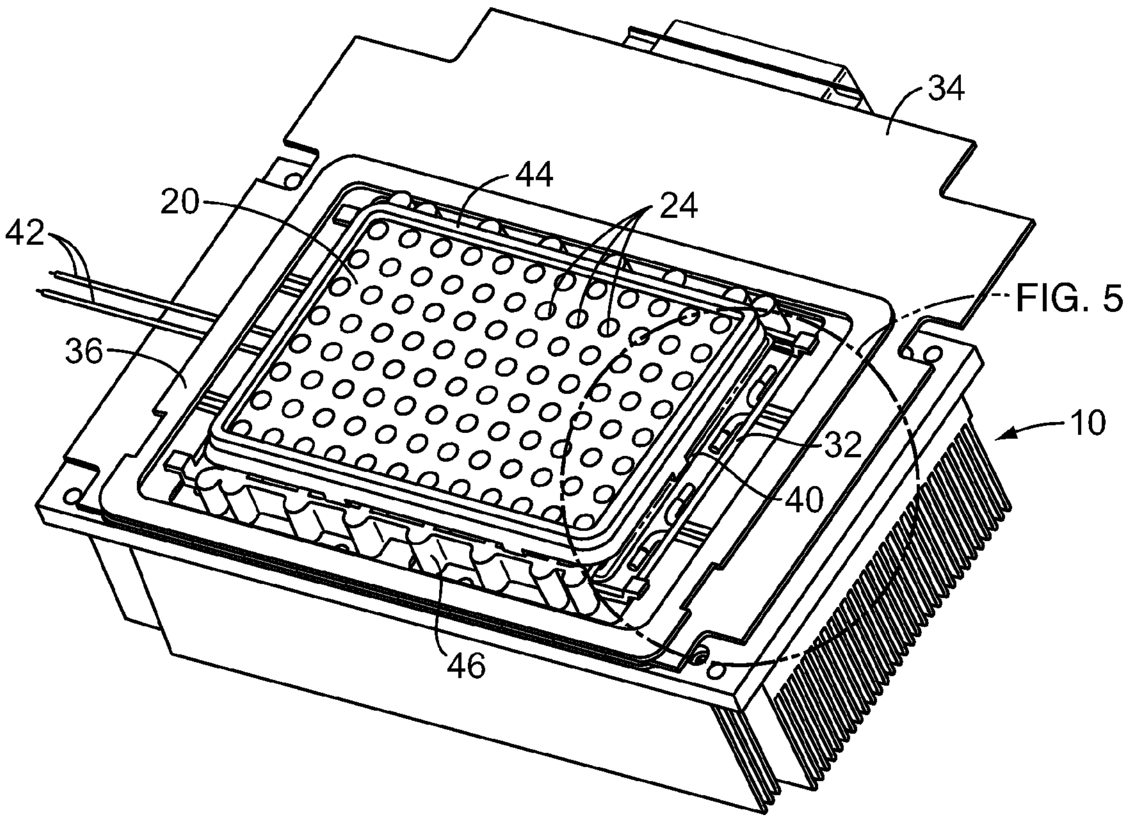
FIG. 4 illustrates various embodiments of a thermal block assembly coupled to a thermoelectric module and heat sink, and coupled to an edge heater.

According to various embodiments, FIG. 3*a* illustrates an edge heater 40. Edge heater 40 can be a resistive heater powered by leads 42 illustrated in FIG. 4. According to various embodiments, edge heater 40 can be positioned around the perimeter of the thermal block assembly 20 such that the edge heater 40 at least partially conforms to the openings 24 closest to the perimeter of the thermal block assembly 20. According to various embodiments, an edge heater can be rectilinear without conforming to the plurality of openings 24. FIGS. 4-5 illustrate edge heater 40 coupled to the perimeter of thermal block assembly 20. Edge heater 40 can be a resistive heater supplied power via leads 42. In this embodiment, FIG. 5 illustrates the coupling of edge heater 40 to the perimeter of thermal block assembly 20 between the bottom 22 and the top 26 of the thermal block assembly 20 and partially around the plurality of openings 24 that are form the sides of thermal block assembly 20. The term "coupled to the perimeter" refers to an edge heater that provides heat from the edges of thermal block assembly. According to various embodiments, edge heaters can be floating around the perimeter of the thermal block assembly on the sides of the plurality of openings 24, top 26 and/or bottom 22. According to various embodiments, edge heater 40 or multiple heaters can provide different power zones to reduce TNU (thermal non-uniformity) during heating.

According to various embodiments, FIG. 4 illustrates the thermal block assembly 20 illustrated in FIG. 2 coupled to the thermoelectric module 30 and heat sink 10 illustrated in FIG. 3. FIG. 5 illustrates a magnified view of this coupling. According to various embodiments, the thermal block assembly 20 overlaps with thermoelectric module 30 such that bottom 22 couples to the surface of thermoelectric module 30. According to various embodiments, either the thermal block assembly 20 or the thermoelectric module 30 can have a larger surface area. Seal 44 can be positioned over thermal block assembly 20 on top 26 to provide a controlled environment surrounding the sample well tray (not shown) positioned to fit into the plurality of openings 24 in the thermal block assembly 20. The seal 44 can reduce the heat diffusion from the thermal block assembly 20 to the environment surrounding the thermal block assembly 20. According to various embodiments, the seal can be constructed of material comprising at least one of EPDM Rubber, Silicone Rubber, Neoprame (CR) Rubber, SBR Rubber, Nitrile (NBR) Rubber, Butyl Rubber, Hypalon (CSM) Rubber, Polyurethane (PU) Rubber, and Viton Rubber.

According to various embodiments, the apparatus for thermal cycling can provide the top 26 of thermal block assembly 20 access to the environment. It can be desirable to protect thermoelectric module 30 from moisture in the environment. Seal 44 can provide a connection between the top 26 of the thermal block assembly 20 and a cover (not shown) that provides a skirt down to gasket 36. The cover (not shown) can isolate the components on top of which it is positioned from the environment. Seal 44 and/or gasket 36 can provide sealing with or without the application of moldable adhesive/sealant, including RTV silicone rubber (Dow Corning).

According to various embodiments, as illustrated in FIG. 4, clamping mechanism 46 provides pressure to couple thermal block assembly 20 to thermoelectric module 30. The clamping mechanism 46 can be constructed to minimize its contact with the thermal block assembly 20 to avoid substantial increase to diffusion of heat. The clamping mechanism 46 can be constructed of glass filled plastic that has sufficient rigidity to provide the desired pressure.

Figure 15:
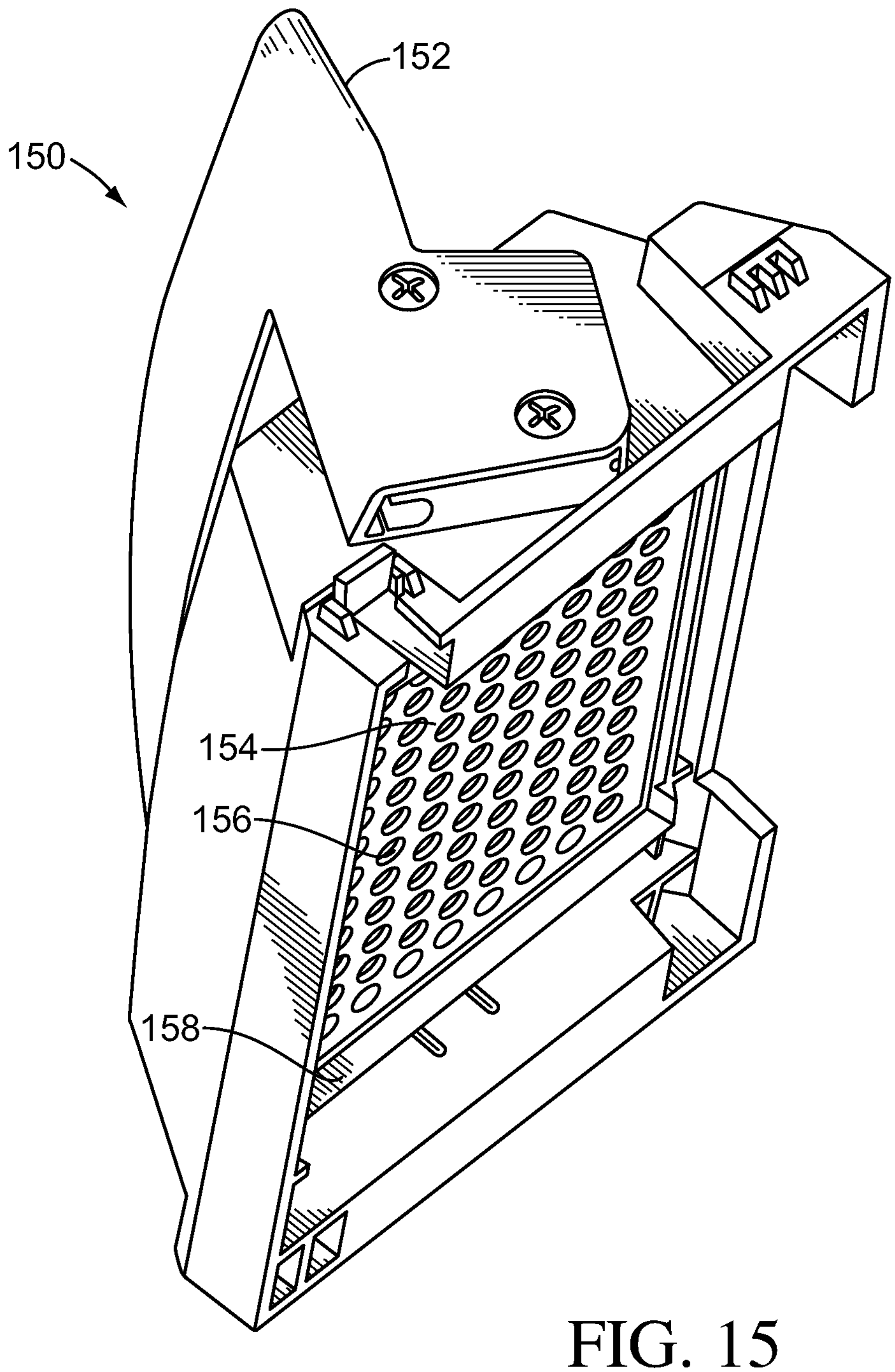
FIG. 15 illustrates various embodiments of a heated cover.

According to various embodiments, as illustrated in FIG. 15, a heated cover 150 can be positioned over the thermal block assembly 20 to provide heating from above. Heated cover 150 can reduce diffusion of heat from the biological samples by evaporation by providing recesses 156 for the caps (not shown) on sample wells (not shown). Heated cover 150 can reduce the likelihood of cross contamination by keeping the insides of the caps dry, thereby preventing aerosol formation when the sample wells are uncapped. Heated cover 150 can maintain the caps above the condensation temperature of the various components of the biological sample to prevent condensation and volume loss of the biological sample. Heated cover 150 can provide skirt 158 around the perimeter of platen 154. According to various embodiments, the heated cover can be of any of the conventional types known in the art. According to various embodiments, heated cover 150 can slide into and out of a closed position by manual physical actuation by handle 152. According to various embodiments, the heated cover can be automatically, physically actuated to and from a closed position by a motor. Heated cover 150 comprises at least one heated platen 154 for pressing against the top surface of the sample well tray. Platen 154 can press down on the sample well tray so that the sample well outer conical surfaces are pressed firmly against the plurality of openings 24 in the thermal block assembly 20. This can increase heat transfer to the sample wells, and can provide temperature uniformity across sample wells in the sample well tray similar to the temperature uniformity across thermal block assembly 20. Platen 154 and skirt 158 can substantially prevent diffusion of heat from thermal block assembly 20. Details of the heated covers and platens are well known in the art of thermal cycling. According to various embodiments, the cover can be not heated.

According to various embodiments, FIG. 5*a* illustrates a cross-section view of edge heater 40 coupled to the thermal block assembly 20 and thermal block assembly 20 coupled to thermoelectric module 30. Thermal diffusivity plate 12 can be positioned within base plate 14. Thermoelectric module 30 can be coupled to thermal diffusivity plate 12 on one side and coupled to thermal block assembly 20 on the other side, powered by lead 38, and lined by frame 32. Thermal block assembly 20 can be coupled to edge heater 40 at the top surface of bottom 22. Seal 44 can be positioned on top 26 of thermal block assembly 20 to line the perimeter of top 26.

Figure 14:
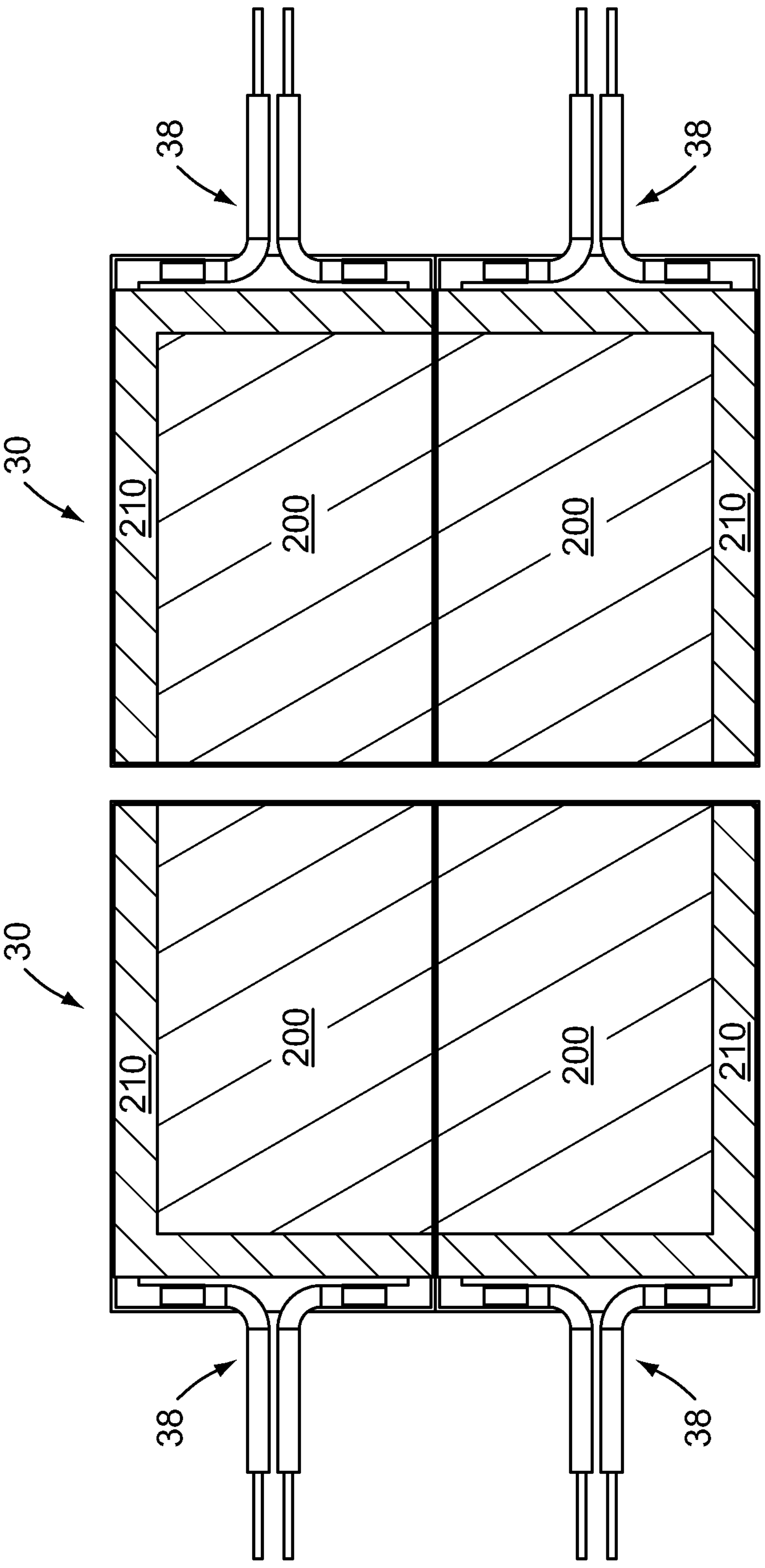
FIG. 14 illustrates various embodiments of a thermoelectric module with different power regions.

According to various embodiments, the thermoelectric module can be configured to provide a variety of heat gradients to minimize TNU. Multiple thermoelectric modules can provide a variety of heat gradients to minimize TNU. According to various embodiments, the thermoelectric module 30 can be configured to provide a constant pumping of heat into thermal block assembly 20 by increasing corner heat flux to minimize TNU as described below. According to various embodiments, as illustrated in FIG. 14, thermoelectric module 30 can comprise two or more Peltier devices that provide different power regions. Leads 38 can provide different power to different Peltier devices producing different power regions. First power region 200 can be coupled to the middle portion of the thermal block assembly, while second power region 210 can be coupled to the perimeter of thermal block assembly to compensate for edge effect. According to various embodiments, the different power regions can provide uniform and non-uniform power regions.

According to various embodiments, TNU can be measured by sampling the temperature at different points on the thermal block assembly. TNU is the non-uniformity of temperature from place to place within the thermal block assembly. According to various embodiments, TNU can be measured by sampling the temperature of the sample in the sample well tray at different openings in the thermal block assembly. Actual measurement of the temperature of the sample in each well in the sample well tray can be difficult because of the small volume in each well and the large number of wells. Temperature can be measured by any method known in the art of temperature control, including a temperature sensor or thermistor.

According to various embodiments, the components of the thermal cycling apparatus can be coupled together with thermal interface media, including thermal grease. According to various embodiments, thermal grease can be positioned at the interface of at least two of the thermal block assembly, the thermoelectric module, thermal diffusivity plate, and the base plate. Thermal grease can avoid the requirement of high pressure to ensure sufficient thermal contact between components. Thermal grease can provide lubrication between expanding and contracting components that are coupled together to decrease wear on the components. Examples of thermal grease include Thermalcote™ II (Aavid Thermalloy, LLC; k=0.699 W/m-K).

According to various embodiments, methods for thermally cycling biological sample can comprise contacting a thermoelectric module to a thermal block assembly; heating the thermal block assembly, wherein the thermal block assembly is adapted for receiving the biological sample; and cooling the thermal block assembly, wherein the cooling comprises diffusing heat to a heat sink with a thermal diffusivity plate. According to various embodiments, thermally cycling the biological sample can comprise contacting said thermal block assembly with an edge heater, wherein the edge heater is coupled to the perimeter of said thermal block assembly. According to various embodiments, thermally cycling the biological sample can provide substantial temperature uniformity to the thermal block assembly. According to various embodiments, diffusing can provide cooling of at least 10° C. in at most ten seconds for said biological sample. According to various embodiments, thermally cycling the biological sample can provide heating and cooling to achieve a PCR cycle time of less than thirty seconds. For example, PCR protocols requiring 30 cycles can be completed in less than fifteen minutes. Various PCR protocols are known in the art of thermal cycling and can include maintaining 4° C. per second temperature ramping up or ramping down.

EXAMPLES

According to various embodiments, the thermal block assembly is heated by ramping up the set point on the temperature controller for the thermal block assembly and is cooled by ramping down the set point on the temperature controller. Following are several examples whose temperature curves are illustrated in FIGS. 6-13. In FIGS. 6-13, the set point temperature curve 60 is associated with the scales on the left vertical axis of the graph indicating temperature in degrees Centigrade and the horizontal axis indicating time in seconds. The time frame in FIGS. 6-13 is an arbitrary block of time in a thermal cycling protocol. In FIGS. 6-13, the thermal non-uniformity curves are associated with the scales on the right vertical axis of the graph indicating TNU in degrees Centigrade and the horizontal axis indicating time in seconds.

Comparative Example 1

Thermal Diffusivity Plate

Figure 6:
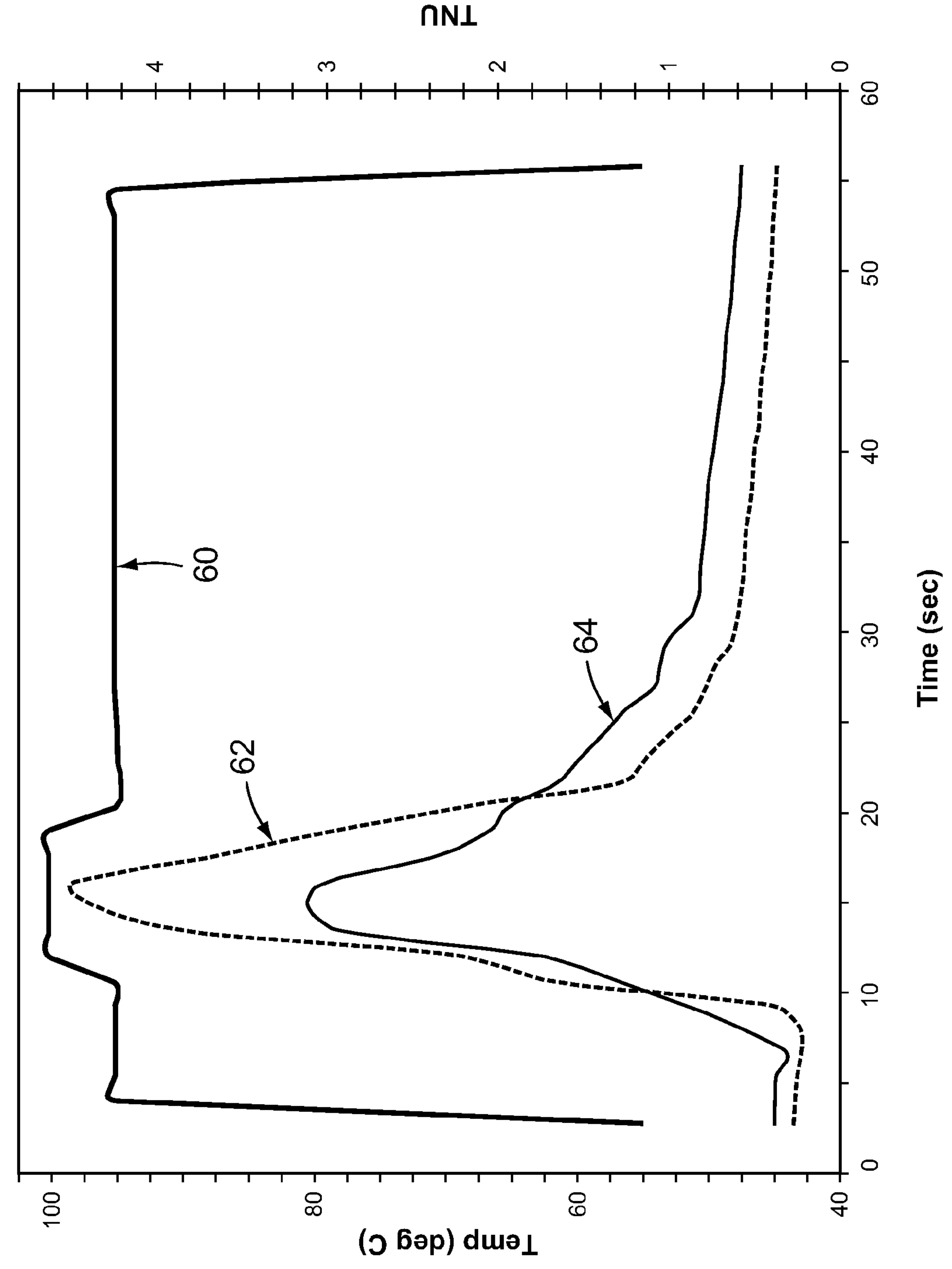
FIG. 6-13 are graph illustrating the temperature curve of the thermal block assembly and thermal non-uniformity of the thermal block assembly for Examples 1-5.
Figure 7:
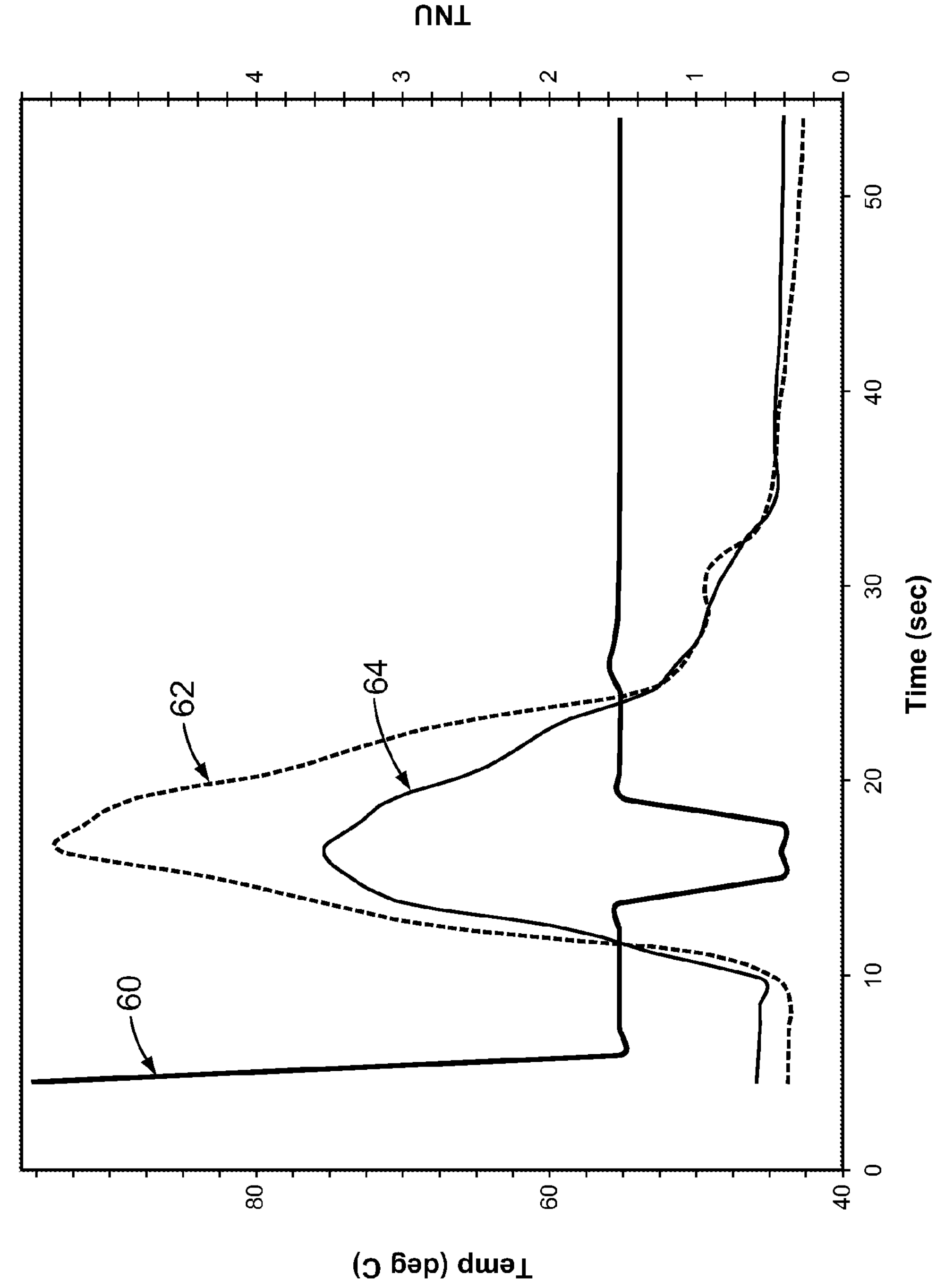

In Example 1, a thermal diffusivity plate constructed of 99.9% EDM copper having a thickness of 8.0 millimeters was coupled to a base plate and pin fins constructed of 6063-T5 aluminum having a thickness of 5.0 millimeters. A thermal block assembly constructed of silver plated with gold was coupled to a thermoelectric device constructed of bismuth telluride. The thermoelectric device was coupled to the thermal diffusivity plate. An edge heater having a power output of 9.3 Watts manufactured by Minco Products, Inc. (Minneapolis, Minn.) was coupled to the thermal block assembly. A seal constructed of silicone rubber was positioned on the top of thermal block assembly. This thermal cycling apparatus was compared to a thermal cycling apparatus similar to the one described above except that the thermal diffusivity plate was replaced with a base plate having a thickness of 13.0 millimeters. FIG. 6 illustrates the temperature curve and TNU curves of the thermal block assembly for ramping up temperature. FIG. 7 illustrates the temperature curve and TNU curves for ramping down temperature. In FIGS. 6-7, the TNU curve 62 relates to the thermal cycling apparatus with the thermal diffusivity plate and TNU curve 64 relates to the thermal cycling apparatus without a thermal diffusivity plate.

Comparative Example 2

Pin Fin and Swage Fin

Figure 8:
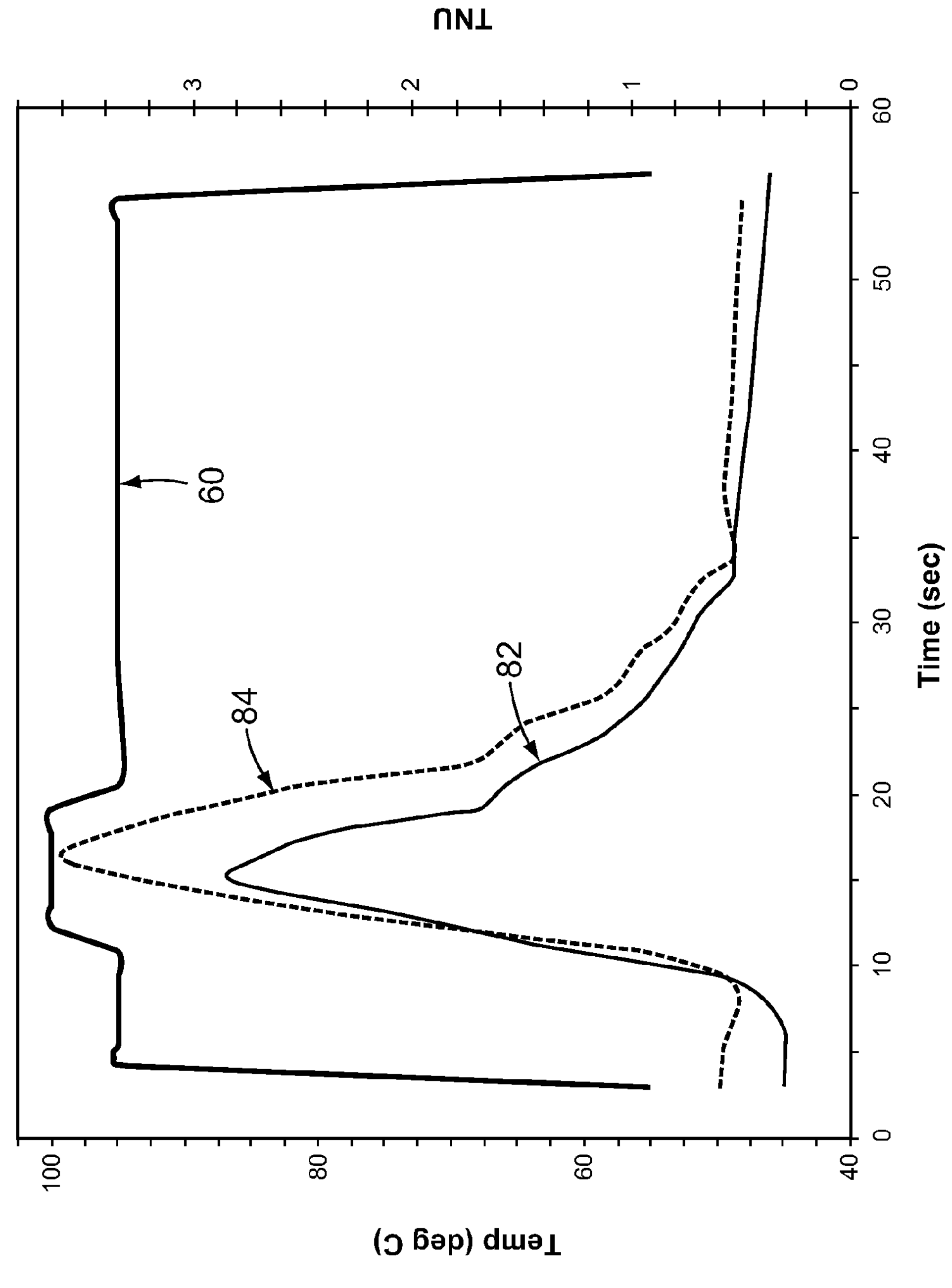
Figure 9:
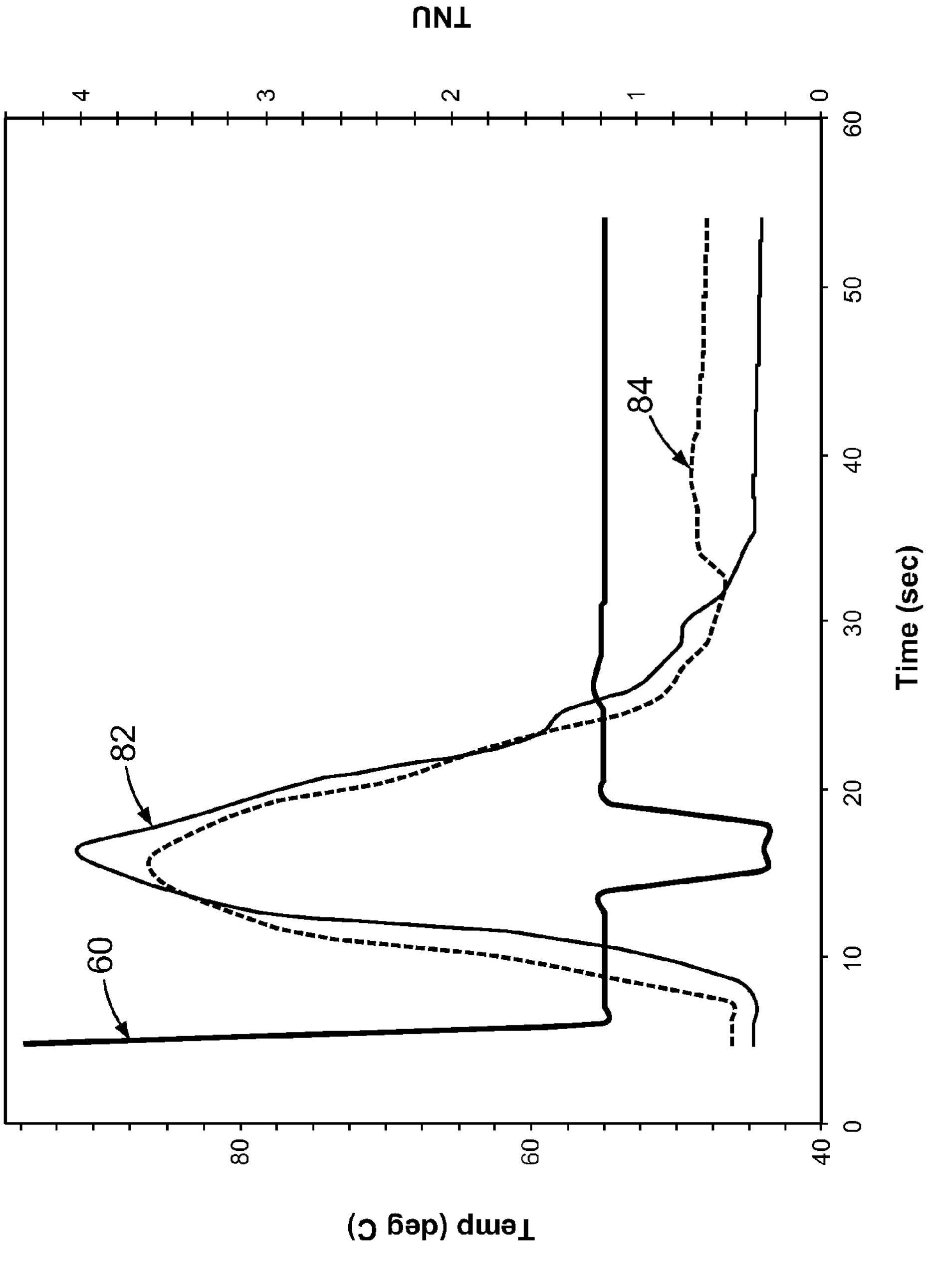

In Example 2, a thermal cycling apparatus with a thermal diffusivity plate similar to the one described in Example 1 was modified to replace the pin fin heat sink with a swage fin heat sink. The thermal cycling apparatus with a thermal diffusivity plate and swage fins was compared to a similar thermal cycling apparatus except that the thermal diffusivity plate was replaced with a base plate having a thickness of 13.0 millimeters. FIG. 8 illustrates the temperature curve and TNU of the thermal block assembly for ramping up temperature. FIG. 9 illustrates the temperature curve and TNU of the thermal block assembly for ramping down temperature. In FIGS. 8-9, the TNU curve 82 relates to the thermal cycling apparatus with a swage fin heat sink and a thermal diffusivity plate and TNU curve 84 relates to the thermal cycling apparatus with a swage fin heat sink without a thermal diffusivity plate.

In Examples 1 and 2, as illustrated by FIGS. 6-9, a thermal diffusivity plate can reduce the TNU during thermal cycling whether a pin fin or swage fin heat sink diffuses heat away from the thermal diffusivity plate. This can be demonstrated by the TNU curves, i.e., TNU curves 62 and 82 reach lower TNU values than TNU curves 64 and 84 after the set point temperature curve 60 reaches the set point near the 20 second mark in FIGS. 6-9.

Comparative Example 3

Multiple Edge Heaters

Figure 10:
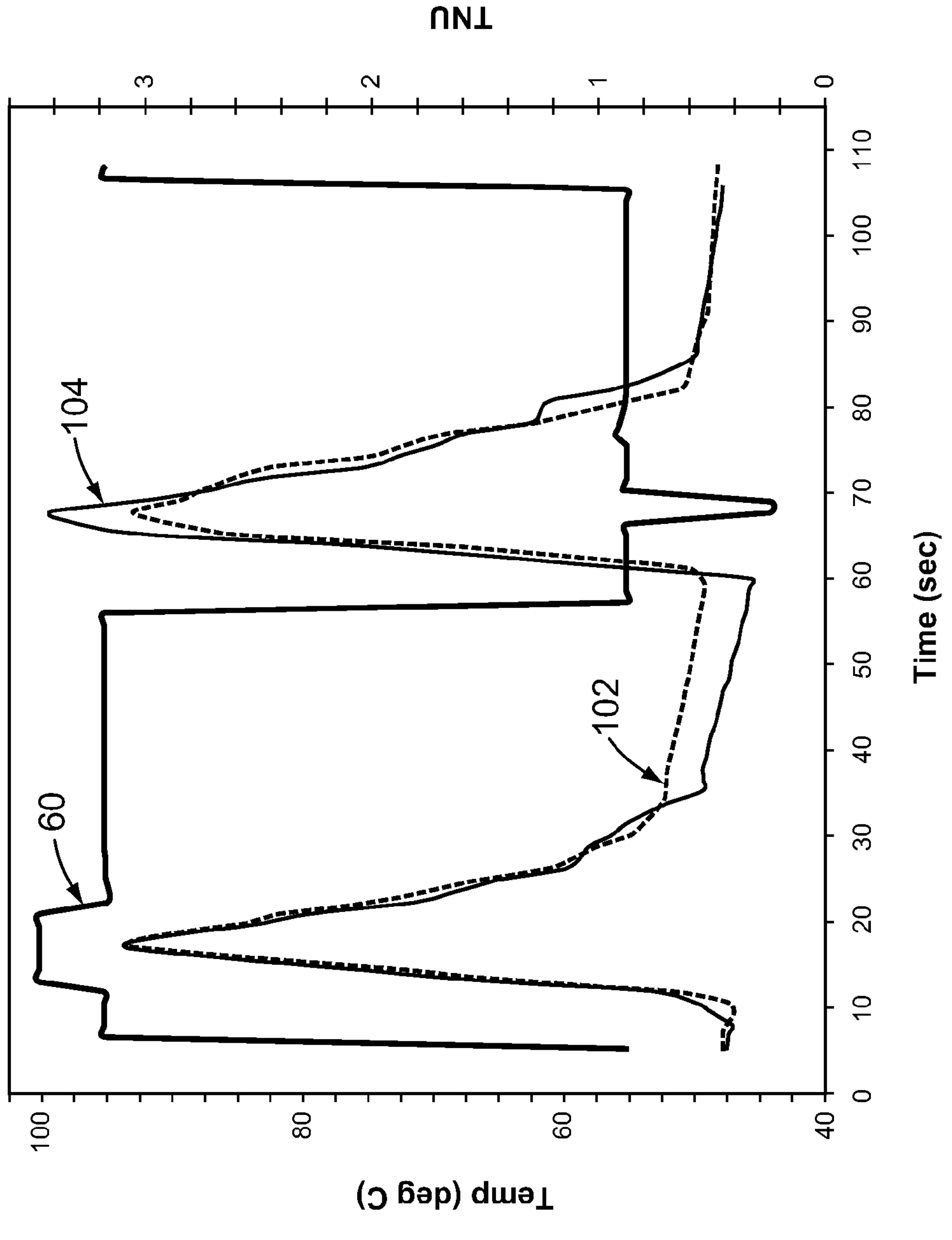
Figure 11:
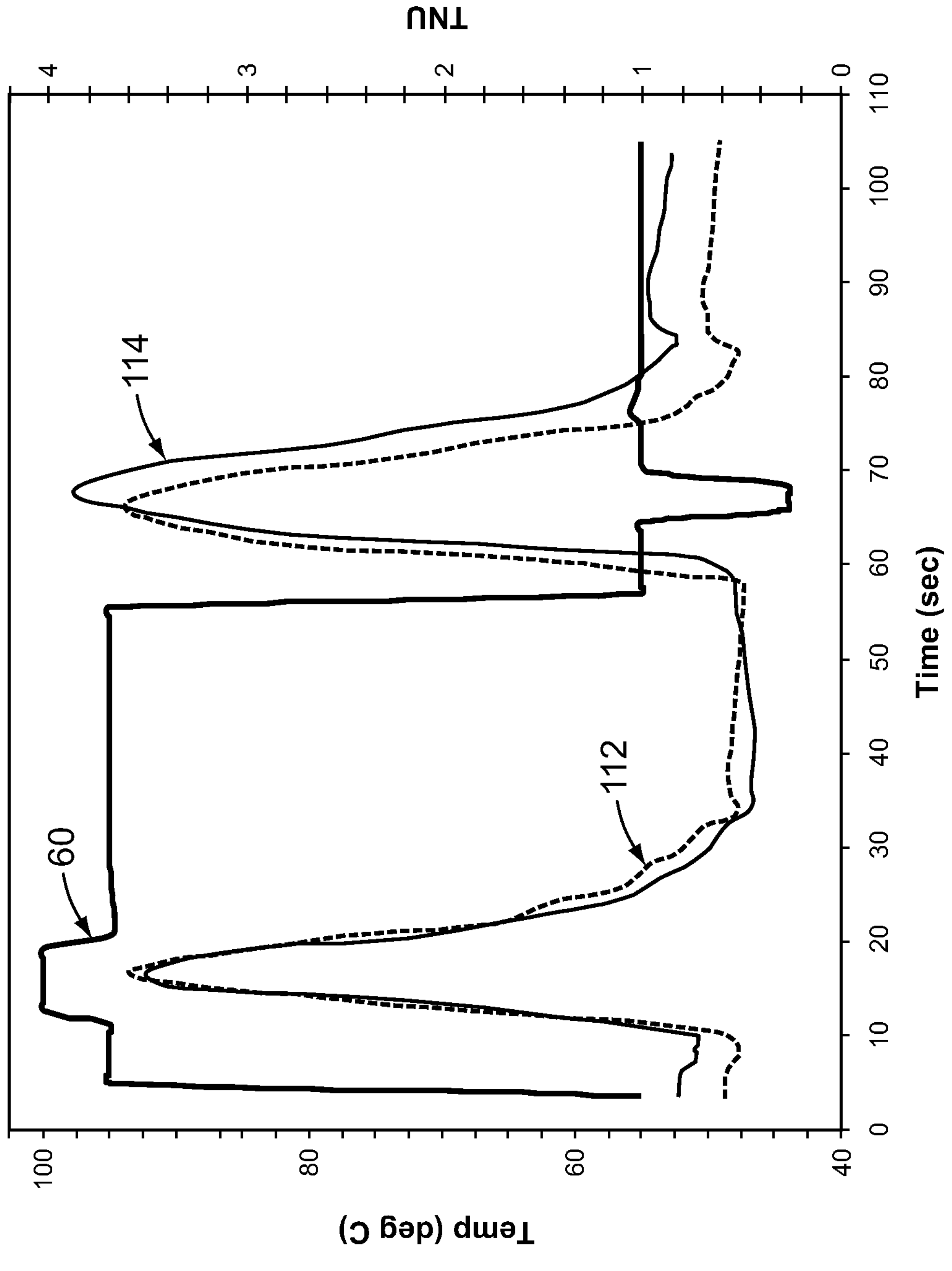

In Example 3, a thermal diffusivity plate constructed of 99.9% EDM copper having a thickness of 8.0 millimeters was coupled to a base plate and fins constructed of 6063-T5 aluminum having a thickness of 5.0 millimeters. A thermal block assembly constructed of silver plated with gold was coupled to a thermoelectric device constructed of bismuth telluride. The thermoelectric device was coupled to the thermal diffusivity plate. An edge heater having a power output of 9.3 Watts manufactured by Minco Products, Inc. (Minneapolis, Minn.) was coupled to the thermal block assembly. A seal constructed of silicone rubber was positioned on the top of thermal block assembly. This thermal cycling apparatus was compared to a thermal cycling apparatus similar to the one described above except that more than one edge heaters was coupled to the thermal block assembly. FIGS. 10-11 illustrate the temperature curve and TNU of the thermal block assembly of varying edge heaters with different fin configurations during thermal cycling. FIG. 10 illustrates a comparison between one and two edge heaters with a pin fin heat sink. TNU curve 102 relates to the thermal cycling apparatus with one edge heater and TNU curve 104 related to the thermal cycling apparatus with two edge heaters. FIG. 11 illustrates a comparison between one and three edge heaters with a swage fin heat sink. TNU curve 112 relates to the thermal cycling apparatus with one edge heater and TNU curve 114 relates to the thermal cycling apparatus with three edge heaters.

Example 3 illustrates that an increased edge heating reduces TNU in heating cycles whether a pin fin or swage fin heat sink diffuses heat away from the thermal diffusivity plate. In the swage fin configuration, additional heat provided by the edge heater during heating increased the TNU during cooling.

Comparative Example 4

Seal

Figure 12:
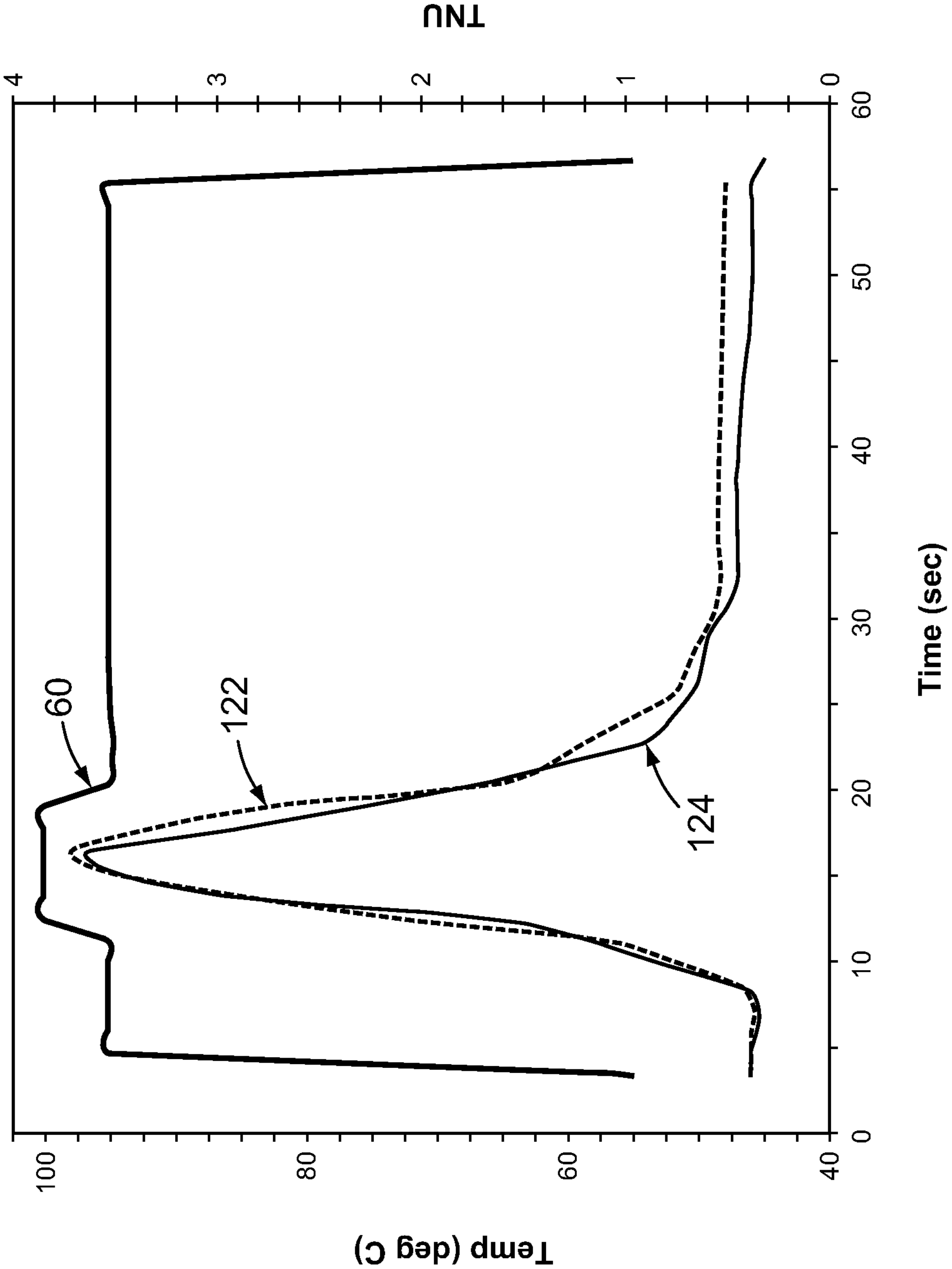
Figure 13:
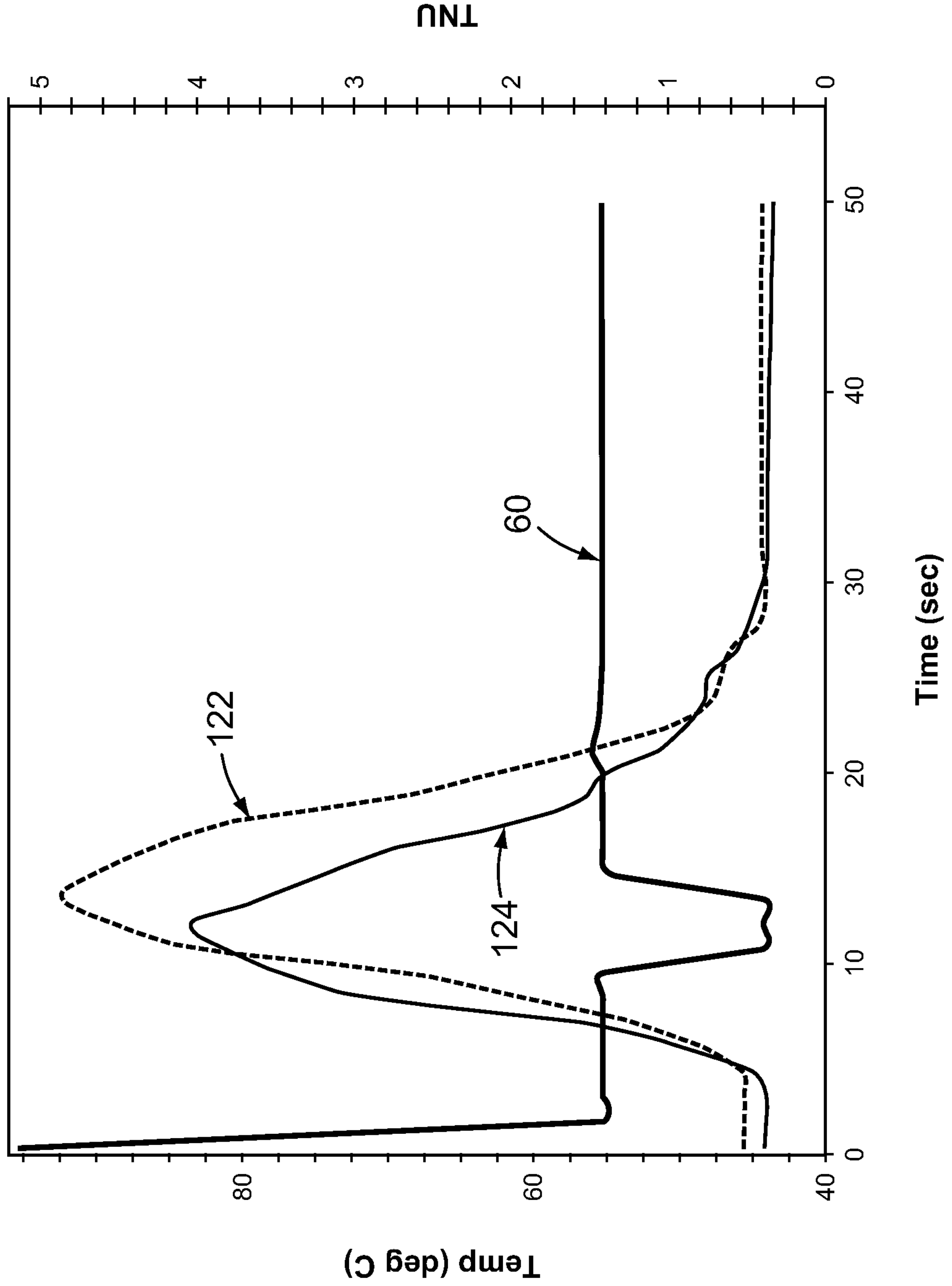

In Example 4, a thermal diffusivity plate constructed of 99.9% EDM copper having a thickness of 8.0 millimeters was coupled to a base plate and pin fins constructed of 6063-T5 aluminum having a thickness of 5.0 millimeters. A thermal block assembly constructed of silver plated with gold was coupled to a thermoelectric device constructed of bismuth telluride. The thermoelectric device was coupled to the thermal diffusivity plate. A seal constructed of silicone rubber was positioned on the top of thermal block assembly. The thermal cycling apparatus described above was compared to a thermal cycling apparatus similar to the one described above except that the seal was removed. FIGS. 12-13 illustrate the temperature curves and TNU curves of the thermal block assembly with a thermal diffusivity plate during thermal cycling. FIG. 12 related to ramping up temperature to the thermal block assembly and FIG. 13 related to ramping down temperature to the thermal block assembly. In FIGS. 12-13, TNU curve 122 relates to the thermal cycling apparatus with a silicon rubber seal and TNU curve 124 relates to the thermal cycling apparatus without a silicon rubber seal.

Example 4 illustrates that a silicon rubber seal can provide a barrier to condensation without significantly affecting the TNU change in a thermal cycling apparatus with a thermal diffusivity plate and pin fin heat sink.

For the purposes of this specification and appended claims, unless otherwise indicated, all numbers expressing quantities, percentages or proportions, and other numerical values used in the specification and claims, are to be understood as being modified in all instances by the term “about.” Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of “less than 10” includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms “a,” “an,” and “the,” include plural referents unless expressly and unequivocally limited to one referent. Thus, for example, reference to “a thermoelectric module” includes two or more thermoelectric modules.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. An apparatus for thermally cycling biological samples comprising:

a thermal block assembly for receiving said biological samples;

a thermoelectric module coupled to said thermal block assembly;

a frame comprising a printed circuit board material positioned around the thermoelectric module and configured to align the thermoelectric module with the thermal block assembly;

a heat sink, wherein said heat sink is coupled to said thermoelectric module with a thermal interface medium, wherein said heat sink comprises a base plate and fins;

a rigid thermal diffusivity plate, wherein said rigid thermal diffusivity plate (a) comprises a different material than said base plate and fins, (b) is positioned between the thermoelectric module and heat sink and contacts the thermoelectric module and the heat sink and (c) is configured to provide temperature uniformity to said thermal block assembly during thermal cycling.

2. The apparatus of claim 1, wherein said thermal diffusivity plate is positioned to couple to said thermoelectric module with the thermal interface medium.

3. The apparatus of claim 1, wherein said thermal block assembly comprises at least one of silver, gold, aluminum, silicon carbide, and magnesium.

4. The apparatus of claim 1, wherein said base plate and fins comprise aluminum.

5. The apparatus of claim 1, wherein said thermoelectric module comprises a thermoelectric gap, wherein said thermoelectric gap provides additional temperature uniformity throughout said thermal block assembly.

6. The apparatus of claim 5, wherein said thermoelectric gap is less than 5 millimeters.

7. The apparatus of claim 1, further comprising an edge heater, wherein said edge heater is coupled to the perimeter of said thermal block assembly.

8. The apparatus of claim 1, wherein said apparatus provides a PCR cycle time of less than thirty seconds.

9. The apparatus of claim 1, wherein said thermoelectric module comprises at least two power regions.

10. The apparatus of claim 1, further comprising a seal positioned on top of said thermal block assembly.

11. The apparatus of claim 1, wherein the thermal interface medium is thermal grease.

12. An apparatus of claim 1, wherein said thermal diffusivity plate is positioned within said base plate.

13. An apparatus of claim 1, wherein said thermoelectric module's horizontal surface area overlaps said thermal diffusivity plate's horizontal surface area.

14. An apparatus of claim 13, wherein said thermoelectric module's horizontal surface area is larger than said thermal diffusivity plate's horizontal surface area.

15. An apparatus of claim 13, wherein said thermal diffusivity plate's horizontal surface area is larger than said thermoelectric module's horizontal surface area.

16. The apparatus of claim 1, wherein the diffusivity plate comprises at least one of copper, silver, gold and silicon carbide.

17. The apparatus of claim 16, wherein the diffusivity plate is copper.

18. The apparatus of claim 3, wherein the copper is 99.9% EDM copper.

19. The apparatus of claim 1, wherein said diffusivity plate is about 8 mm thick.

20. The apparatus of claim 1, wherein the diffusivity plate has a thermal capacity greater than silver, gold or magnesium.

21. An apparatus for thermally cycling biological samples comprising:

a thermal block assembly for receiving said biological samples;

a thermoelectric module capable of heating and cooling, wherein the thermoelectric module is coupled to said thermal block assembly;

a printed circuit board positioned around the thermoelectric module and configured to align the thermoelectric module with the thermal block assembly;

a heat sink;

a frame positioned around the thermoelectric module; and a rigid thermal diffusivity plate comprising copper coupled to said thermoelectric module with a thermal interface medium and coupled to said heat sink, wherein said rigid thermal diffusivity plate is positioned between said thermoelectric module and said heat sink, has at least 25% greater thermal diffusivity than said heat sink and is configured to provide temperature uniformity to said thermal block assembly during thermal cycling.

22. The apparatus of claim 21, wherein the temperature uniformity provides cooling of at least 10° C. in at most ten seconds for said thermal block assembly.

23. The apparatus of claim 21, wherein said thermal block assembly comprises silver and gold.

24. The apparatus of claim 21, wherein said thermoelectric module comprises a thermoelectric gap, wherein said thermoelectric gap provides additional temperature uniformity throughout said thermal block assembly.

25. The apparatus of claim 24, wherein said thermoelectric gap is less than 5 millimeters.

26. The apparatus of claim 21, further comprising an edge heater, wherein said edge heater is coupled to the perimeter of said thermal block assembly.

27. An apparatus of claim 21, wherein said thermal interface medium is thermal grease.

28. An apparatus of claim 21, wherein said thermoelectric module's horizontal surface area overlaps said thermal diffusivity plate's horizontal surface area.

29. An apparatus of claim 28, wherein said thermoelectric module's horizontal surface area is larger than said thermal diffusivity plate's horizontal surface area.

30. An apparatus of claim 28, wherein said thermal diffusivity plate's horizontal surface area is larger than said thermoelectric module's horizontal surface area.

31. An apparatus of claim 21, wherein said thermal diffusivity plate is positioned within a base plate of said heat sink.

32. An apparatus for thermally cycling biological samples comprising:

a thermal block assembly for receiving biological samples;

a thermoelectric module in direct contact with a printed circuit board and coupled to said thermal block assembly;

a frame positioned around the thermoelectric module and configured to align the thermoelectric module with the thermal block assembly;

a heat sink, wherein said heat sink is coupled to said thermoelectric module with a thermal interface medium, wherein said heat sink comprises a baseplate and fins, is structured and arranged to provide a heat sink uniformity to the block assembly;

a rigid thermal diffusivity plate, wherein said rigid thermal diffusivity plate comprises a different material from the baseplate and fins, is positioned between the thermoelectric module and heat sink, structured and arranged to provide temperature uniformity to said thermal block assembly during thermal cycling, and wherein the rigid thermal diffusivity plate has a thickness less than the baseplate; and wherein the uniformity provided by the diffusivity plate is greater than the heat sink thermal uniformity at an at least one specified point during a thermal cycle.

33. The apparatus of claim 32, whereby the at least one specified point in the thermal cycle is an at least one specified region during the thermal cycle.

34. The apparatus of claim 33, wherein the at least one specified region is a setpoint region of the thermal cycle.

35. The apparatus of claim 34, wherein the setpoint region is a steady state region of the thermal cycle.

* * * * *